US00RE35743E

United States Patent [19]

Pearson

[11] E Patent Number: Re. 35,743

[45] Reissued Date of Patent: Mar. 17, 1998

[54] PATIENT MEDICATION DISPENSING AND ASSOCIATED RECORD KEEPING SYSTEM

[75] Inventor: Walter G. Pearson, Pineville, La.

[73] Assignee: Pearson Ventures, L.L.C., Alexandria, La.

[21] Appl. No.: 609,730

[22] Filed: Mar. 1, 1996

Related U.S. Patent Documents

Reissue of:

[64] Patent No.: 5,292,029
Issued: Mar. 8, 1994
Appl. No.: 751,916
Filed: Aug. 29, 1991

U.S. Applications:

[63] Continuation-in-part of Ser. No. 433,256, Nov. 8, 1989, abandoned, which is a continuation-in-part of Ser. No. 242,585, Sep. 12, 1988, abandoned.

[51] Int. Cl.[6] ..... G07F 11/00

[52] U.S. Cl. ..... 221/2; 221/9; 221/123; 312/209; 364/479

[58] Field of Search ..... 221/211, 2, 3, 221/9, 15, 123, 131, 79; 414/280, 266

[56] References Cited

U.S. PATENT DOCUMENTS

| | | | |
|---|---|---|---|
| 2,684,783 | 7/1954 | Ahlstrom | 221/258 |
| 3,334,784 | 8/1967 | Morrison | 221/7 |
| 3,467,277 | 9/1969 | Tolliver | 221/264 |
| 3,848,112 | 11/1974 | Weichselbaum et al. | 235/61.7 R |
| 3,892,489 | 7/1975 | Wdzieczkowski | 356/157 |
| 3,917,045 | 11/1975 | Williams et al. | 194/4 |
| 4,018,358 | 4/1977 | Johnson et al. | 221/7 |
| 4,141,461 | 2/1979 | LaChance | 220/253 |
| 4,267,942 | 5/1981 | Wick et al. | 221/2 |
| 4,473,884 | 9/1984 | Behl | 364/479 |
| 4,546,901 | 10/1985 | Buttarazzi | 221/10 |
| 4,655,026 | 4/1987 | Wigoda | 53/55 |
| 4,664,289 | 5/1987 | Shimizu et al. | 221/2 |
| 4,674,651 | 6/1987 | Scidmore et al. | 221/3 |
| 4,674,652 | 6/1987 | Aten et al. | 221/3 |
| 4,695,954 | 9/1987 | Rose et al. | 364/413 |
| 4,733,362 | 3/1988 | Haraguchi | 364/479 |
| 4,785,969 | 11/1988 | McLaughlin | 221/2 |
| 4,832,229 | 5/1989 | Hackman et al. | 221/25 |
| 4,847,764 | 7/1989 | Halvorson | 364/413.02 |
| 4,853,521 | 8/1989 | Claeys et al. | 235/375 |

(List continued on next page.)

OTHER PUBLICATIONS

Ser. No. 08/598574, Pearson, Feb. 12, 1996.
Ser. No. 08/502118, Pearson, Jul. 13, 1995.

*Primary Examiner*—Kenneth Noland
*Attorney, Agent, or Firm*—Robert K. Rhea; John H. Runnels

[57] ABSTRACT

[In a nurse administered medication dispensing system a mobile cart contains a plurality of doctor prescribed medication in accordance with a like plurality of patients scheduled to receive such medication. The medication containers stored in the cart is accessible by the nurse only in response to a patient ID code entered by the nurse into the keyboard of a cart supported microprocessor including a software program responding to the input code energizing mechanical components which obtains the medication from an onboard supply and transfers it to a specified nurse accessible cubicle or which releases secured medication dispensing units on or in the cart and records the time, date and quantity of medication dispensed.]*A fully automatic apparatus for dispensing medications in tablet or capsule form for a patient is disclosed. This apparatus includes several open containers to hold tablets or capsules, with the location of each container fixed relative to the apparatus, and with the containers not readily accessible to an unauthorized person. The apparatus also includes a computer programmed to correlate a patient's identity with the medications that are appropriate for the patient. The computer controls a carrier that moves to the location of each of the containers holding medication appropriate for the patient. The carrier retrieves the medication from each such container, and then releases the medication in a location where it may readily be retrieved by a human to administer to the patient.*

6 Claims, 3 Drawing Sheets

U.S. PATENT DOCUMENTS 4,911,327 3/1990 Shepherd et al. ..... 221/3
4,939,705 7/1990 Hamilton et al. ..... 368/10
4,967,928 11/1990 Carter ..... 221/2
4,971,221 11/1990 Urquhart et al. ..... 221/2
5,097,982 3/1992 Kedem et al. ..... 221/3
5,292,029 3/1994 Pearson ..... 221/2
5,405,048 4/1995 Rogers et al. ..... 221/211
5,490,610 2/1996 Pearson .

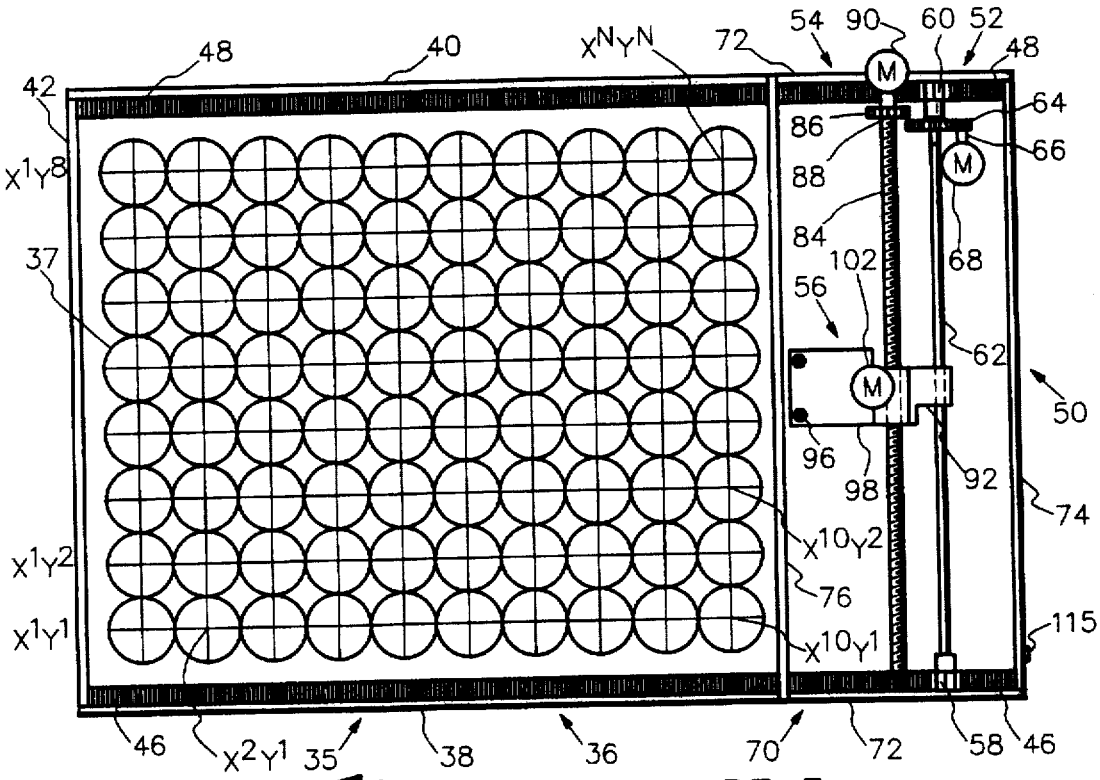
FIGURE 3
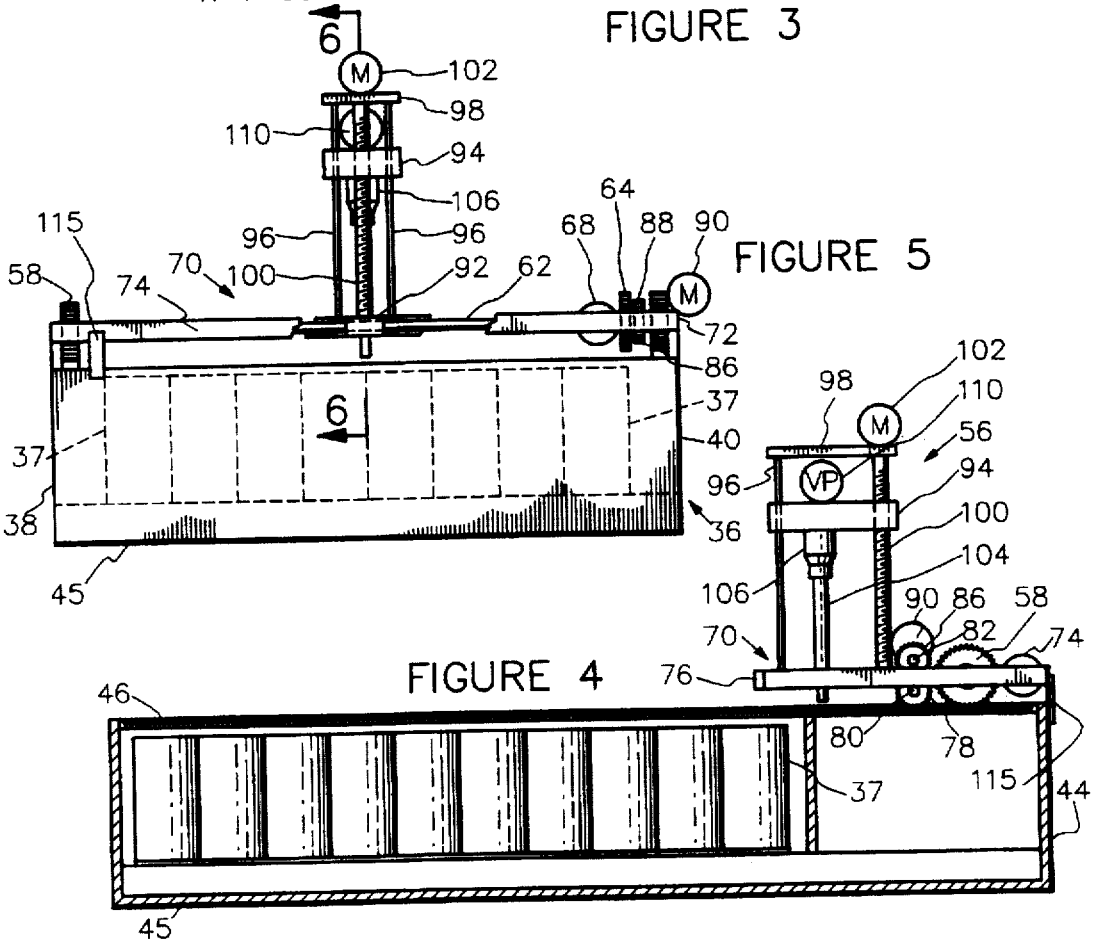
FIGURE 5
FIGURE 4

PATIENT MEDICATION DISPENSING AND ASSOCIATED RECORD KEEPING SYSTEM

Matter enclosed in heavy brackets [ ] appears in the original patent but forms no part of this reissue specification; matter printed in italics indicates the additions made by reissue.

CROSS REFERENCE TO RELATED [APPLICATION] *APPLICATIONS*

This application is *a reissue of an application filed by me in the U.S. Patent and Trademark Office on Aug. 29, 1991, under Ser. No. 07/751,916, now U.S. Pat. No. 5,292,029, issued Mar. 8, 1994, which is* a continuation-in-part of an application filed by me in the U.S. Patent and Trademark Office on Nov. 8, 1989, under Ser. No. 07/433,256 now abandoned for Patient Medication Dispensing and Associated Record Keeping System[.], *which is a continuation-in-part of an application filed by me in the U.S. Patent and Trademark Office on Sep. 12, 1988, under Ser. No. 07/242, 585, abandoned, for Patient Medication Dispensing and Associated Record Keeping System.*

BACKGROUND OF THE INVENTION

1. Field of the Invention

This invention relates to nursing care and more particularly to an electronic medication dispensing, accounting and record keeping system of patients in a hospital-type facility.

In some hospitals or clinics a serious problem frequently occurs when medication or treatment is performed on the wrong patient. Such problems may arise when the person dispensing or administering prescription drugs or injections or taking fluid samples identifies the patient by writing the patient's name and/or ID number on a slip of paper and for a variety of reasons, such as the transfer of patients to different beds and errors in marking the information on the slip of paper the wrong patient may be given the medication or treatment.

It is common practice for hospitals and other patient care facilities to maintain a patient identification system, usually comprising a temporary bracelet on the patient's arm, which contains his name and/or ID number. Unfortunately many times this identification is not cross referenced by the nurse or technician administering the treatment. In accordance with this invention, a unique identification system is disclosed in which the patient ID number is entered into the system record keeping apparatus in order to obtain doctor prescribed medication or other items necessary for the required treatment of the patient.

This cross check of patient and medication or treatment is recorded and transmitted to a designated central control station.

2. Description of the Prior Art

Prior patents generally disclose apparatus and systems for patent identification and correlation with doctor's orders and medication administering or laboratory results obtained.

Similarly, other prior patents provide a patient fluid input and output record to insure patient fluid balance.

U.S. Pat. No. 3,848,112 is an example of a patient identification system in which a coded ID bracelet, applied to the patient upon admission, is later utilized by programmed circuitry to identify and correlate drugs, the quantity thereof and/or treatment being administered to the patient which insures treatment of the proper patient.

This invention is distinctive over the above named patent by providing a nurse actuated mobile station which accompanies the nurse or technician on their rounds and which dispenses drug medication or treatment medication in response to the nurse entering a particular patient's identification data in the mobile station input facility which responds by dispensing doctor prescribed medication or treatment instructions.

SUMMARY OF THE INVENTION

A manually moved upright mobile vehicle contains a plurality of medication storage and dispensing units accommodating the physical properties of the [mediation] *medication* and/or instruments to be used and an onboard microprocessor equipped with software, a keyboard and connectable with a modem and printer all energized by an onboard source of electrical energy and operated by programmed software in response to operator supplied input commands at the keyboard. Electronic circuitry connects the microprocessor with and activates mechanical units in a predetermined sequence for a selected one of several dispensing medication units corresponding to the patient identification entered into the computer by the nurse on duty.

A primary function of the system is to control and restrict medication dispensing, to the types and quantities specified in advance by the pharmacist, doctor, supervisor, or other authorized personnel. This provides accuracy and eliminates pilferage. The software, together with the dispensing apparatus, restricts the dispensing to only those medications determined in advance.

The medication dispensing nurse cannot normally obtain [mediation] *medication* from the apparatus that was not previously scheduled for that time and patient, thus increasing accuracy and minimizing drug pilferage.

The principal object of this invention is to insure dispensing correct medication or treatment to individual patients by correlating the patient's ID with the software operating a computer which automatically records the data, such as medication dispensed, time, patient's ID and other data, thus relieving nursing personnel from such record keeping and minimizing human error.

BRIEF DESCRIPTION OF THE DRAWINGS

FIG. 3 is a top view, to a different scale, of a tablet or capsule dispenser;

FIG. 4 is a side elevational view of FIG. 3;

FIG. 5 is a right end view of FIG. 4; and,

DESCRIPTION OF THE PREFERRED EMBODIMENTS

Figure 1:
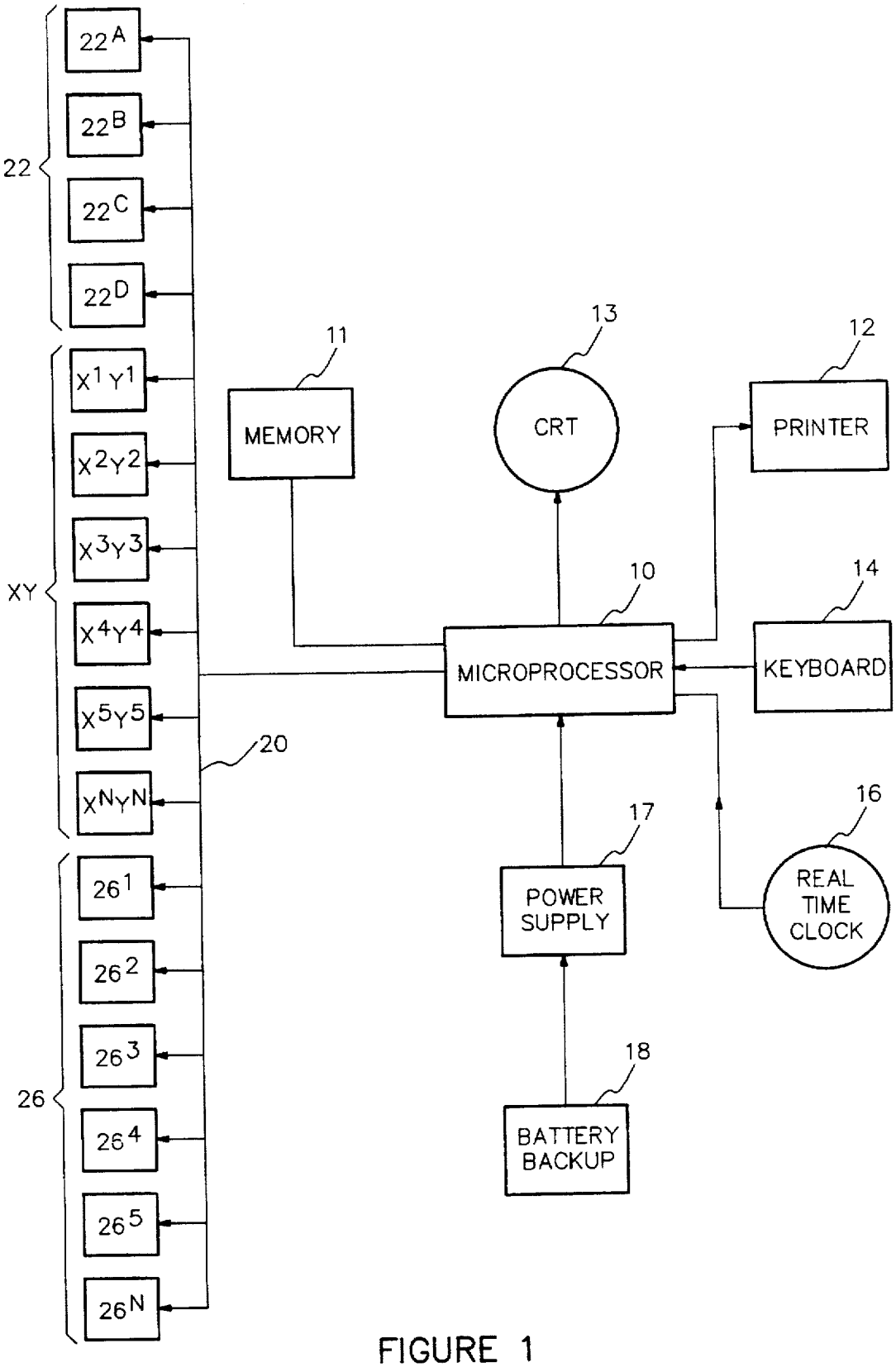
FIG. 1 is a flow diagram.

Like characters of reference designate like parts in those figures of the drawings in which they occur.

In the drawings:

Referring more particularly to FIG. 1, the basic elements of a medical electronic accounting system in accordance with the present invention are illustrated. The system includes a software program which supplies data in digital form to a digital computer which acts on this data to yield output signals activating medication dispensing units in conformance with operator input data previously supplied by authorized expert personnel and activated by medical nurse personnel on duty. The bus-oriented characteristic of the computer allows connecting numerous devices to the computer as long as the formal organization of the communication data is the same as that required by the bus and read by the computer.

All digital computers essentially comprise a minicomputer or microcomputer including a central processing unit, CPU, indicated by the reference numeral 10, having a memory system and some form of input/output control. The purpose of the central processing unit is to receive and store data for later processing in a memory 11 in the form of bits or binary digits in accordance with previous program instructions or data to obtain results which are sent through the bus to control peripheral devices and also delivered through a readout unit such as a printer 12 and a cathode ray tube CRT 13.

The central processing unit (CPU) performs the arithmetic and the logic operations under the supervision of a software system which monitors information from an input/output (I/O) port, such as a keyboard 14, a real time clock 16 and feedback through the bus from the hereinafter described peripheral devices, including the CRT 13.

The memory components 11 contain data and instruction codes including a file or unique addresses correlating physical devices, as hereinafter described, with their corresponding mechanisms.

Figure 2:
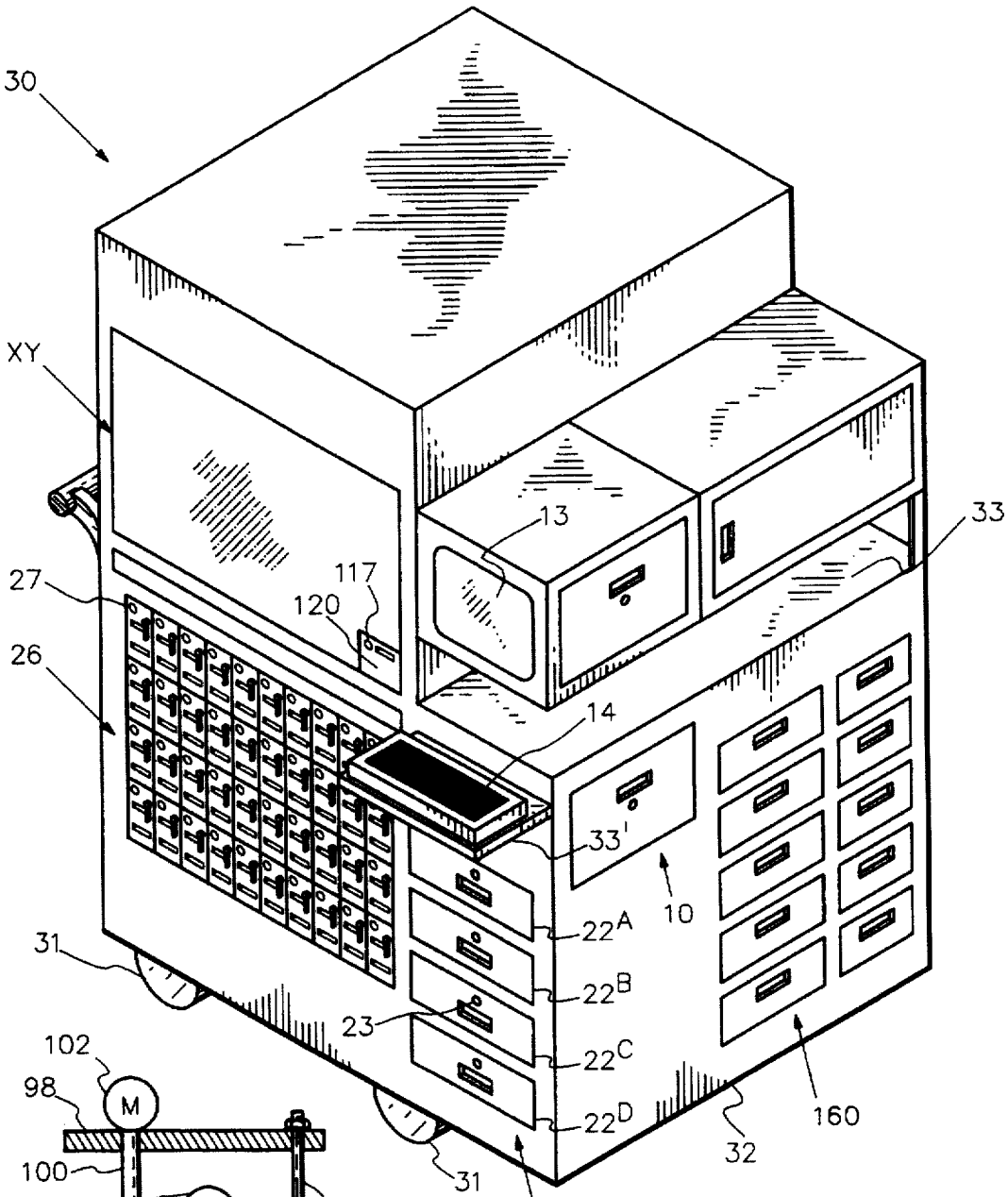
FIG. 2 is an isometric view of a mobile medication dispensing unit.
Figure 6:
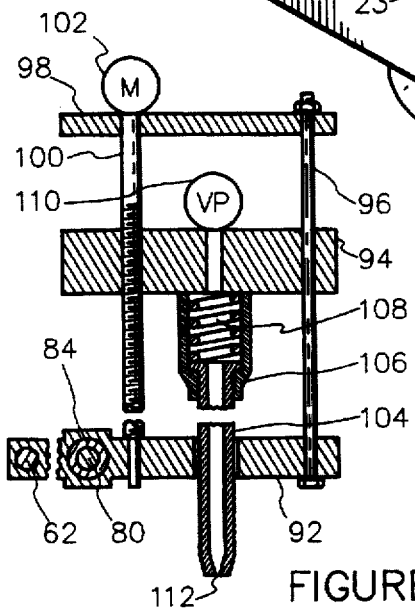
FIG. 6 is a fragmentary vertical cross sectional view to a larger scale taken substantially along the line 6—6 of FIG. 5.

As is well known, the capability of a computer is dependent upon the storage capacity of its memory which may range from fewer than 100 bits as in pocket calculators to approximately a billion bits in large scale computers. The "hardware" components of a digital computer are the central processing unit (CPU), the memory system and the input/output devices. The control registers and the arithmetic logic unit of the CPU are linked with the memory system and the input/output devices, unique to this system, through a data bus 20 allowing the memory, the CPU and the I/O devices to operate and monitor a plurality of peripheral components, such as a series of drawers 22, a tablet/capsule dispenser area XY and a series of door closed cubicles or compartments 26 (FIG. 2). In the present example, in addition to an onboard rechargeable source of electric energy 17 powering the digital computer and its connected peripheral devices, a lithium battery 18 backs up memory 11 to ensure that the memory is nonvolatile and will continue to store data in the event of a power interruption from the energy source 17.

The reference numeral 30 indicates the mobile unit hereinafter referred to as "cart" which is upright rectangular in overall configuration supported by a plurality of wheels 31 which may be swivelling casters for manually manipulating the cart around obstacles such as may be encountered in a hospital ward. Intermediate its height, the forward end 32 of the cart is provided with a substantially horizontal platform forming a workshelf 33 including a laterally extending pull-out section 33'.

The computer keyboard and numeric key pad 14 are supported by the shelf 33'. The keyboard 14 is connected with the microprocessor 10 which is contained by the cart in a forward compartment and operatively connected with the monitor or CRT 13 so that images on its screen may easily be visualized by the nurse when at the keyboard. The lower front end portion and rearward portion of the cart supports and provides access to the plurality of medication dispensing drawers 22, tablet/capsule dispenser unit XY and cubicles or compartments 26.

Referring also to the remaining FIGS., the numeral 35 indicates a tablet/capsule dispenser unit contained by the cart area XY.

The unit 35 comprises an upwardly open rectangular box-like frame 36 formed by upstanding side walls 38 and 40 and end walls 42 and 44, joined by a bottom wall 45.

The major portion of the area encompassed by the side and end walls of the box frame 36 is filled with a plurality of rows of upwardly open containers 37 extending longitudinally between the end walls 42 and 44 and transversely between the side walls 38 and 40. The vertical axis of each container being represented by a point on a rectangular Cartesian coordinate system ranging from $X^1Y^1$ to $X^NY^N$.

The side wall 38 and the end wall 42, respectively, represent the positive portion X and Y axes of a rectangular Cartesian coordinate system for locating and dispensing a tablet or capsule from a selected one of the containers, as will now be explained.

The upper limit of the box frame side walls 38 and 40 longitudinally support a pair of [racks] *tracks* 46 and 48 along which a gantry-type carriage system 50 is movable.

The carriage 50 comprises an X axis propulsion means 52, a Y axis propulsion means 54 and a Z axis propulsion means 56.

The X axis means 52 comprises a pair of spur gears 58 and 60 axially secured to an axle 62 and movable along the pair of racks 46 and 48 by angular rotation of the axle 62. A driven spur gear 64 is axially secured to the axle 62 adjacent the spur gear 60. The spur gear 64 is driven by a pinion 66 on the drive shaft of a reversible motor 68. The motor 68 is supported by a rectangular platform frame 70 horizontally supported above the racks 46 and 48 by bearings journalling the end portions or the axle 62 and movable longitudinally of the box frame 36 therewith. The frame 70 comprises side members 72 and end members 74 and 76.

The forward or left-end of the frame 70, as viewed in FIGS. 3 and 4, is supported by idler spur gears 78 journalled by bearings 80 secured to and depending from the respective frame side members 72 for supporting the carriage 50 in its to and fro movement along the racks 46 and 48. An axle shaft 82 (FIG. 4) extends between the idler gears 78 for the purposes presently explained.

The Y axis means 54 comprises an exteriorly threaded tube 84 which surrounds and is substantially coextensive with and is journalled by the axle shaft 82. A spur gear 86 surrounds the screw tube 84 at one of its ends and is driven by a pinion 88 secured to the drive shaft of a reversible motor 90 for angular rotation of the screw tube 84.

The screw tube 84 threadedly extends through an end portion of a Z axis platform support 92. The support 92 has its other end portion slidably surrounding the axle 62 for Y axis movement of the motor support 92 transversely of the box frame 36.

The Z axis means 56 comprises a horizontal platform 94 vertically slidable along a plurality of parallel upright standards 96 supported at their depending ends by the support 92 and interconnected at their upper ends by a horizontal motor mount 98.

The horizontal platform 94 threadedly surrounds an intermediate portion of a screw shaft 100 angularly rotated by a reversible motor 102 on the motor mount 98 having its drive shaft connected with the upper end thereof. The platform 94 further supports vertically disposed elongated telescoping tubes 104 and 106 normally telescopically extended and depending from the platform 94 by a spring means 108 for the purposes presently explained.

A motor driven vacuum pump 110 is mounted on the platform 94 and is operatively connected with the uppermost telescoping tube 106 to produce a pressure reduction at the depending preferably relatively small open end 111 of the lower tube 104 for the purpose of lifting and transporting a capsule or tablet, not shown, as presently explained.

Obviously, some patients require medication or treatments other than standard tablets or capsules, to this end the series of drawers or cubicles 26 are individually designated by one of the numerals $26^1$ through $26^N$.

OPERATION

In operation, assuming the cart 30, drawers, cubicles and dispenser unit has been loaded with medication and the nurse and cart is at a patient's bedside. The nurse inputs the patient's ID into the keyboard 14 and the computer acting in response to the software energizes the lamps 23, 27 or 117 of the particular drawer or cubicle containing the medication for the identified patient.

When the medication is in one of the containers designated by the XY Cartesian coordinate numerals, the software, via the computer, energizes the X and Y axis means 52 and 54 to position the vertical axis of the lowermost vacuum tube 104 on the vertical axis of the selected tablet or capsule container.

The Z axis motor 102 is then energized to angularly rotate the screw 100 for lowering the platform 94 and the tube 104 into the selected container while simultaneously the vacuum pump 110 is energized to draw air into and through the tubes 104 and 106.

When the depending open end 112 of the tube 164 contacts a tablet or capsule in the selected container, the spring 108 cushions the impact of the tube 104 with the tablet so that the latter will not be crushed while simultaneously a rapid increase of pressure reduction in the tube triggers the vacuum pump sensor, not shown, to energize the X and Y axes means 52 and 54 to return to the home position (adjacent the frame side wall 38 and end wall 44) where the frame 70 end wall 76 contacts an upstanding microswitch 115, supported by the box frame end wall 44, to deenergize the vacuum pump. This releases the capsule or tablet, not shown, into the XY unit access drawer 120 and simultaneously energizes its light 117.

There is a role played by the medication nurse. The on-the-spot dispensing nurse verifies that there is no mistake in the medication dispensed by comparing the CRT display and the printed (hard copy) reminding the medication nurse to examine and verify the medication. In this way the system provides a redundancy subsystem to enhance accuracy.

There are some occasions in which the cart must allow the medical nurse to request a medication that was not scheduled in advance. This can happen, for example, in an emergency, or if one or more of the dispensed tablets is accidentally dropped. For such cases, the software allows emergency requests without defeating the general restriction, by automatically recording the emergency or special problem request and the identification code of the personnel who requested it.

In this way, the software, via its locking and unlocking of the dispensing devices and the feedback from the devices to the cart, constituting the only way in which medication dispensing can occur with this system, guarantees responsibility and accountability for any necessary specific exceptions to general restrictions. In this way the combination controlled dispensing devices combined regulation and order with necessary flexibility and accountability.

Obviously the invention is susceptible to changes or alterations without defeating its practicability. Therefore, I do not wish to be confined to the preferred embodiment shown in the drawings and described herein.

I claim:

[1. An electronic medication dispensing and accounting system for use in nurse car facilities to ensure correlation of doctor prescribed medication with individual patients and provide a running account of all medications dispensed to patients, comprising:

digital computer having a monitoring means coupled thereto;

a computer access panel;

mobile unit means including a compartmentalized medication containing enclosure supporting said computer and a source of electrical energy;

circuit means including a plurality of data I/O channels coupling the access panel to the computer;

plurality of medication container means in said mobile unit means including a plurality of upwardly open containers disposed in rows along the X and Y axes of an X, Y and Z axes rectangular Cartesian coordinate system;

gantry-like carriage means including mobile means movable along the respective X, Y and Z axes of the Cartesian coordinates;

pressure reduction means supported by the Z axis mobile means for moving medication from a selected said open container to a predetermined release position in response to software generated signals operating in conformance with manually supplied preprogrammed input data; and, medication monitoring means connecting said motor driven mobile means with said circuit means.]

[2. The medication accounting system according to claim 1 and further including:

an upwardly open box frame having a bottom wall for containing said container means, said box frame having opposing side and end walls, one said side wall and one said end wall respectively defining the X and Y axes.]

[3. The medication accounting system according to claim 2 in which the X axis carriage means includes:

a pair of racks longitudinally supported by said box frame side walls;

a horizontal support frame having opposing side and end members;

an axle extending between and journalled by said support frame side members;

a rack supported spur gear on the respective end of said axle;

rack supported idler spur gears journalled by said support frame side members forwardly of the first said spur gears for maintaining the plane of said support frame horizontal; and, X axis motor means drivably connected with one spur gear of said spur gears for moving said support frame longitudinally along said racks.]

[4. The medication accounting system according to claim 3 in which the Y axis carriage means includes:

an axle shaft extending axially between said idler spur gears;

a coextensive externally threaded tube journalled by said axle shaft;

a first platform having one end portion threadedly received by said threaded tube and having an opposite end portion slidably supported by said axle;

spur gear teeth surrounding one end portion of said threaded tube; and,

Y axis motor means drivably connected with said tube spur gear teeth for angular rotation of said threaded tube and moving said platform between said support frame side members.]

[5. The medication accounting system according to claim 4 in which the Z axis carriage means includes:

a plurality or standards vertically supported by said first platform;

a motor mount extending between the upper limit of said standards;

an externally threaded shaft extending vertically between and journalled by said first platform and said motor mount;

a second platform surrounding an intermediate portion of the threaded shaft and slidably guided by said standards;

Z axis motor means for angularly rotating said threaded shaft and vertically reciprocating said second platform;

a motor driven vacuum pump supported by said second platform; and, a plurality of telescoping tubes vertically depending from and operatively connected with said vacuum pump for removing a tablet or capsule from a selected container of said plurality of containers.]

*6. An apparatus for dispensing appropriate medications in tablet or capsule form to a patient, comprising:*

*(a) a compartment adapted to house a plurality of containers for holding medications in tablet or capsule form, wherein each location of the compartment for housing a container is fixed relative to the apparatus, and wherein said compartment is not readily accessible to an unauthorized person;*

*(b) a computer adapted to be programmed to correlate a patient's identity with the medications that are appropriate for the patient at the time;*

*(c) a carrier responsive to said computer, wherein said carrier is adapted to move under the control of said computer to the location for each container that holds a medication appropriate for the patient, then to create a partial vacuum to retrieve the medication from each appropriate container, and then to release the partial vacuum and place the retrieved medication where it may readily be retrieved by a human to administer to the patient.*

*7. An apparatus as recited in claim 6, additionally adapted to house a plurality of second containers for holding medications not in tablet or capsule form.*

*8. An apparatus as recited in claim 6, wherein said computer is additionally programmed to maintain a record of all medications administered to each patient.*

*9. An apparatus for dispensing appropriate medications in tablet or capsule form to a patient, comprising:*

*(a) a compartment adapted to house a plurality of containers for holding medications in tablet or capsule form; wherein, with respect to a hypothetical rectangular x, y, z-Cartesian coordinate system superimposed on said apparatus, in which the z-direction is vertical, said compartment is adapted to house a plurality of containers that are accessible along the z-direction; wherein each location of the compartment for housing a container is fixed relative to the apparatus, with the fixed locations regularly spaced with respect to one another in both the x-direction and the z-direction; and wherein said compartment is not readily accessible to an unauthorized person;*

*(b) a computer adapted to be programmed to correlate a patient's identity with the medications that are appropriate for the patient at the time;*

*(c) a carrier responsive to said computer, wherein said carrier is adapted to move above the containers under the control of said computer to the x and y coordinates of each of the containers that holds a medication that is appropriate for the patient, then to lower a retrieval device along the z-direction into each appropriate container to retrieve medication from that container, and then to release the retrieved medication where it may readily be retrieved by a human to administer to the patient.*

*10. An apparatus as recited in claim 9, wherein said retrieval device is adapted to create a partial vacuum to retrieve medication from the appropriate containers, and then to release the partial vacuum and to place the medication where it may readily be retrieved by a human to administer to the patient.*

*11. An apparatus as recited in claim 9, wherein said computer is additionally programmed to maintain a record of all medications administered to each patient.*

* * * * *